(12) United States Patent
Duckett et al.

(10) Patent No.: US 11,941,573 B2
(45) Date of Patent: *Mar. 26, 2024

(54) FOOD TRACEABILITY SYSTEM AND METHOD

(71) Applicant: Avery Dennison Retail Information Services LLC, Mentor, OH (US)

(72) Inventors: Jeanne Duckett, Franklin, OH (US); Michael Schaberl, Munich (DE); Txus Carrion, Bayern (DE)

(73) Assignee: Avery Dennison Retail Information Services LLC, Mentor, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/295,320

(22) Filed: Apr. 4, 2023

(65) Prior Publication Data
US 2023/0245040 A1 Aug. 3, 2023

Related U.S. Application Data

(62) Division of application No. 16/723,027, filed on Dec. 20, 2019, now Pat. No. 11,657,361.

(Continued)

(51) Int. Cl.
*G06Q 10/0833* (2023.01)
*G01N 33/02* (2006.01)
(Continued)

(52) U.S. Cl.
CPC ......... *G06Q 10/0833* (2013.01); *G01N 33/02* (2013.01); *G06Q 10/087* (2013.01);
(Continued)

(58) Field of Classification Search
CPC ............. G06Q 10/0833; G06Q 10/087; G06Q 30/0623; G06Q 50/28; H04W 4/35; G01N 33/02
(Continued)

(56) References Cited

U.S. PATENT DOCUMENTS

| 2004/0100380 A1 | 5/2004 | Lindsay et al. |
| 2007/0293980 A1 | 12/2007 | Gudjonsson et al. |

(Continued)

FOREIGN PATENT DOCUMENTS

| CN | 101299248 | 11/2008 |
| CN | 101982833 | 3/2011 |

(Continued)

OTHER PUBLICATIONS

"Labeling in Food Industries—a Marketing Strategy" Published by University of Brasov (Year: 2012).*

(Continued)

*Primary Examiner* — Zeina Elchanti

(57) ABSTRACT

A system and method for food traceability from a food service location to the consumer is disclosed. The method comprises marking food items with a received label as the food items are received. This received label identifies a storage location for the food item and generates traceability information for the food item. If the food item is not intended for storage, then the food item is transferred to a prep table and unique item information is generated for the food item. The food item can then be prepped for usage. During the prepping process, the food item's expiration date is verified, and a serial number is generated, and a use by date is calculated. If the prepped food item is to be served to a consumer, a label is generated with traceability information, and unneeded ingredients are re-purposed or properly disposed of.

22 Claims, 19 Drawing Sheets

Related U.S. Application Data

(60) Provisional application No. 62/782,739, filed on Dec. 20, 2018.

(51) Int. Cl.
  *G06Q 10/087* (2023.01)
  *G06Q 30/0601* (2023.01)
  *G06Q 50/28* (2012.01)
  *H04W 4/35* (2018.01)

(52) U.S. Cl.
  CPC ......... *G06Q 30/0623* (2013.01); *G06Q 50/28* (2013.01); *H04W 4/35* (2018.02)

(58) Field of Classification Search
  USPC .......................................................... 705/333
  See application file for complete search history.

(56) References Cited

U.S. PATENT DOCUMENTS

| | | | | |
|---|---|---|---|---|
| 2008/0223929 | A1* | 9/2008 | Togashi | G06Q 10/00 235/385 |
| 2008/0300993 | A1* | 12/2008 | Rozenblatt | G06Q 30/06 705/16 |
| 2009/0319362 | A1* | 12/2009 | Dashnaw | G06Q 30/02 705/14.34 |
| 2009/0327104 | A1 | 12/2009 | Sanders et al. | |
| 2013/0105565 | A1 | 5/2013 | Kamprath | |
| 2013/0273509 | A1 | 10/2013 | Mutti | |
| 2014/0122519 | A1* | 5/2014 | Jung | G06Q 10/00 707/769 |
| 2014/0244526 | A1* | 8/2014 | Georges | G06Q 30/018 705/317 |
| 2015/0310385 | A1* | 10/2015 | King | G06Q 10/087 705/28 |
| 2016/0267416 | A1 | 9/2016 | Hodges | |
| 2017/0228760 | A1* | 8/2017 | Mason-Gugenheim | G06Q 20/3276 |
| 2017/0284733 | A1* | 10/2017 | Chiu | G06V 10/56 |

FOREIGN PATENT DOCUMENTS

| | | |
|---|---|---|
| CN | 102800023 | 11/2012 |
| CN | 103942671 | 7/2014 |
| CN | 104331768 | 2/2015 |
| CN | 104599041 | 5/2015 |
| CN | 105550833 | 5/2016 |
| CN | 106022796 | 10/2016 |
| JP | 2005-196507 | 7/2005 |
| WO | 2007/140018 | 12/2007 |
| WO | 2016/114808 | 7/2016 |
| WO | 2018/125131 | 7/2018 |

OTHER PUBLICATIONS

International Preliminary Report on Patentability dated Jun. 16, 2021 issued in corresponding IA No. PCT/US2019/067906 filed Dec. 20, 2019.

International Search Report and Written Opinion dated Feb. 26, 2020 issued in corresponding IA No. PCT/US2019/067906 filed Dec. 20, 2019.

"EU Meat and Poultry Traceability Implementation Guideline, Physical Product and Information Flow," GS1 in Europe, The Global Language of Business, Release 0.9, Jun. 26, 2015, 27 pages. https://gs1lv.org/upload/Bukleti/EU_meat_and_poultry_traceability_implementation_guideline.pdf.

"Fresh Fruit and Vegetable Traceability Guideline, Implementing traceability in fresh fruit & vegetable supply chains using the GS1 standards for identification, data capture, data sharing & the GS1 Global Traceability Standard," GS1, The Global Language of Business, Release 2.0, Feb. 2021, 107 pages. https://www.gs1.org/docs/traceability/Global_Traceability_Implementation_Fresh_Fruit_Veg.pdf.

* cited by examiner

| 102 | 104 | 106 | 108 | 110 | 112 | 114 | 116 | 118 | 120 |
|---|---|---|---|---|---|---|---|---|---|
| VENDOR ITEM NUMBER | GTIN14 | SUPPLIER NAME | ITEM DESCRIPTION | STORAGE LOCATION | ORDER UNIT | STORED UNITS | SHELF LIFE | INNER PACKS | WEIGHT |

| EVENT TYPE | RECEIVING DATE | SSCC | GLN (RECEIVE TO) | GLN (RECEIVE) EXT | ORIGINAL GLN | GLN EXT | GTIN | COMPANY | PRODUCT LOT | PRODUCT SERIAL NUMBER | PRODUCT QUANTITY UNITS | PRODUCT QUANTITY AMOUNT | BEST BEFORE DATE (BEST BEFORE DATE) | EXPIRATION DATE (EXPIRATION DATE) | PACK DATE (PACK DATE) | OPERATOR |
|---|---|---|---|---|---|---|---|---|---|---|---|---|---|---|---|---|
| MONIT-ORING | 181108 | NA | 08171380150017 | | 00817138010005 | | 00817138010005 | VPREP | 0011108 | 1 | 1 | CASE | 181113 | 181120 | 181108 | KATHY |

SHIP TO STORAGE DRY STORAGE LARGE

| SHIPPING | 181108 | NA | 08171380150024 | | 00817138015017 | | 00817138010005 | VPREP | 0011108 | 1 | 1 | CASE | 181113 | 181120 | 181108 | KATHY |
| RECEIVING | 181108 | NA | 08171380150024 | | 00817138015017 | | 00817138010005 | VPREP | 0011108 | 1 | 1 | CASE | 181113 | 181120 | 181108 | KATHY |

| 902 | 904 | 906 | 908 | 910 | 912 | 914 | 916 | 918 |
|---|---|---|---|---|---|---|---|---|
| INPUT VENDOR ITEM NUMBER | GTIN14 | ITEM DESCRIPTION | STORAGE LOCATION | PREP UNITS | STORED UNITS | STORED UNITS | INNER PACKS | WEIGHT |

| EVENT | DATE | GLN | GLN EXTENSION | GTIN (INPUT) | PRODUCT LOT (INPUT) | PRODUCT SERIAL NUMBER (INPUT) | PRODUCT QUANTITY UNITS (INPUT) | PRODUCT QUANTITY AMOUNT (INPUT) | GTIN OUTPUT | PRODUCT LOT OUTPUT | PRODUCT SERIAL NUMBER (OUTPUT) | PRODUCT QUANTITY UNITS (OUTPUT) | PRODUCT QUANTITY AMOUNT (OUTPUT) | PRODUCTION DATE (PRODUCTION DATE) | RETURNABLE ASSET NUMBER | RETURNABLE ASSET NUMBER EXT | OPERATOR |
|---|---|---|---|---|---|---|---|---|---|---|---|---|---|---|---|---|---|
| TRANSF-ORMING | 181108 | 081713-8015062 | | 081713-8010005 | 0011108 | 1 | CASE | 1 | | | | | | | | | KATHY |
| TRANSF-ORMING | 181108 | 081713-8015062 | | 081713-8010012 | 0011108 | 1 | CASE | 1 | | | | | | | | | KATHY |
| TRANSF-ORMING | 181108 | 081713-8015062 | | | | | | | 081713-8010319 | 0020108 | 1 | BAG | 1 | 1108 | | | KATHY |

UNITI CAFE

1504 — CHICKEN + BRUSSELS

ROASTED CHICKEN, ROASTED BRUSSELS SPROUTS, ROASTED SWEET POTATOES, LOCAL APPLES, RAW WALNUTS, ORGANIC MESLUN, CHOPPED ROMAINE

DRESSING

CRANBERRY MAPLE VINAIGRETTE

CONTAINS - DAIRY

1506 — NUTRITION FACTS
SERVINGS PER CONTAINER 1

AMOUNT PER SERVING
CALORIES 425   CALORIES FROM FAT 47

1502

Scan Me

(01) 0 081713801000 5
EXP DATE NOV 20, 18
LOT 0011114 SERIAL NO 843

REAL FOOD
+
REAL PEOPLE

1600

NUTRITION FACTS — 1602

INGREDIENT SOURCE — 1604

LOT INFORMATION — 1606

FOOD TRACEABILITY SYSTEM AND METHOD

CROSS REFERENCE TO RELATED APPLICATION(S)

The present application is a division of U.S. application Ser. No. 16/723,027 filed Dec. 20, 2019, and claims priority to and the benefit of U.S. Patent Application No. 62/782,739 filed Dec. 20, 2018, both of which are incorporated herein by reference in entirety.

BACKGROUND

The present invention relates generally to a traceability system and, more specifically, to a traceability system and method for food product items. The traceability system of the present invention allows for traceability of the food product item from its generation to its ultimate delivery to a consumer, donation center or disposal site, and provides transparency into the socio and environmental impacts of the food products. The system of the present invention is particularly suitable for food products prepared within a restaurant or other food service location, such as a bar, mobile kitchen, hotel, soup kitchen, etc. Accordingly, the present specification makes specific reference thereto. However, it is to be appreciated that aspects of the present invention are also equally amenable to other like applications and devices.

The need for food traceability from the kitchen to the consumer is becoming increasingly self-evident. Every day seems to bring a new food recall. There are also growing environmental, socio-economic and ethical issues and concerns surrounding the amount of food waste occurring on a daily basis. For example, it has been reported that Americans alone waste as much as 150,000 tons of food each day, and that, annually, the wasted food was grown on the equivalent of over 30 million acres of cropland, or approximately 7.5% of all harvested cropland in the United States.

Additionally, today's consumers are becoming increasingly concerned about food product transparency and the socio and environmental impacts of said food product items. While there has been literature written about the need for traceability in the foodservice industry, there are no practical implementations of tracing food from its generation or preparation through to the consumer or the ultimate disposal of the food product. Several reasons for the lack of a practical solution exist.

First, the skill level and available time of the average foodservice worker is relatively limited, thereby reducing the potential of using complex food traceability systems that require multiple steps. Second, available food traceability technology in the kitchen and other food preparation locations is somewhat limited and typically consists of manual processes requiring the careful recording of information, use of color dots, and finally transcribing the information into a digital record, all of which is not only time consuming, but cost prohibitive and prone to human error.

Therefore, there exists in the art a long felt need for a system or method of tracing food products from their origin (e.g., a kitchen or other food preparation location) to their delivery to a consumer or the ultimate disposal of the food product. Having the ability to trace food products from their origin to their ultimate destination will enable governments, companies and individuals in the food production chain to improve the overall quality and safety of food product items, reduce hunger and food waste, and improve overall efficiencies and the sustainability of valuable resources used in the food product production process.

Generally stated, the system and method of the present invention comprises marking food product items with a received label as the food items are prepared or received. The received label identifies the current storage location for the food product item, and generates traceability information for the food product item going forward. If the food product item is not intended for storage at its current location, then the food product item is transferred to a preparation or prep table and unique item information is generated for the food product item or ingredient. The food product item is then prepped for usage. For example, during the prepping process the food product item's expiration date may be verified, a serial number may be generated, and/or a "use by", "best by" and/or expiration date may be calculated. If the prepped food product item is to be served to a consumer, a label may also be generated with traceability information, and any unneeded ingredients may be re-purposed or properly disposed of.

As discussed herein, external traceability refers to the ability to record and retain the what, where, when, and why each action was taken in a food product lifecycle from supply chain partner to supply chain partner, and internal traceability refers to the product path for a supply chain participant covering commissioning or receiving through to transformation, consumption, disposal, or shipment of the food product to the next partner.

SUMMARY

The following presents a simplified summary in order to provide a basic understanding of some aspects of the disclosed innovation. This summary is not an extensive overview, and it is not intended to identify key/critical elements or to delineate the scope thereof. Its sole purpose is to present some concepts in a simplified form as a prelude to the more detailed description that is presented later.

The subject matter disclosed and claimed herein, in one aspect thereof, comprises a method for food traceability from a food product preparation or food service location to the consumer, storage or ultimate disposal of the food product item. General stated, the method comprises marking the food product item with a label and storing data from the label for subsequent retrieval. Then, as food items are received, a subsequent received label may be printed for the food product item. The received label identifies a storage location for the food product item, and generates traceability information for the food product item. The food product item can then be prepped for usage. For example, during the prepping process, the food product item's expiration date may be calculated or verified, and the food product item may be weighed. A serial number is then generated and a "use by", "best by" or expiration date may be calculated for the prepped food product item.

If the prepped food product item is to be immediately served to a consumer, a label is generated with traceability information, and any unneeded ingredients from the prepped food product item are stored, re-purposed or properly disposed of. If the prepped food product item is not to be immediately served to a consumer, then a shipping label is printed and the prepped food is available for immediate storage or shipment to a desired location.

In an alternative embodiment of the present invention, if the food product item is not intended for storage, then the food product item is transferred to a prep table and unique item information is generated for the food product item.

Further, when the food product item's expiration date is verified and determined to be past the expiration date, the prepped food item may be processed as donated food or waste and properly disposed of.

Alternatively, if the prepped food product item is not to be immediately served to a consumer or shipped, then the food product item may be stored. If the prepped food product item is stored, a storage label may be generated for it. The storage label preferably comprises a quick response (QR) code, or other printed code, e.g. bar code, 2D code, and scanning the QR code allows a user to access traceability information about the food product item from a web page. Alternatively, the storage label may be comprised of a barcode, radio-frequency identification (RFID) tag, label or inlay. In addition, the packaging may include an embedded RFID tag without the need to apply the tag via a label to the package.

In an alternative embodiment of the present invention, the food traceability method comprises a user receiving a food product item and generating a unique identifier number and a serial number for the food product item. The user then assigns the unique identifier number and the serial number to the food product item, and also assigns a "use by", expiration date and/or any other useful information to the food product item. Furthermore, a label is then generated with traceability information for the food product item. Typically, traceability information is encoded within a QR code or other suitable code as is known in the art, such as a barcode, RFID tag, etc.

To the accomplishment of the foregoing and related ends, certain illustrative aspects of the disclosed innovation are described herein in connection with the following description and the annexed drawings. These aspects are indicative, however, of but a few of the various ways in which the principles disclosed herein can be employed and is intended to include all such aspects and their equivalents. Other advantages and novel features will become apparent from the following detailed description when considered in conjunction with the drawings.

BRIEF DESCRIPTION OF THE DRAWINGS

FIG. 1 illustrates an example of preconfigured data in accordance with the disclosed architecture.

FIG. 4 illustrates an example of food product event related data in accordance with the disclosed architecture.

FIG. 9 illustrates one example of preconfigured prep item table data in accordance with the disclosed architecture.

FIG. 11 illustrates a perspective view of event data generated for transformation in accordance with the disclosed architecture.

DETAILED DESCRIPTION

Figure 2:
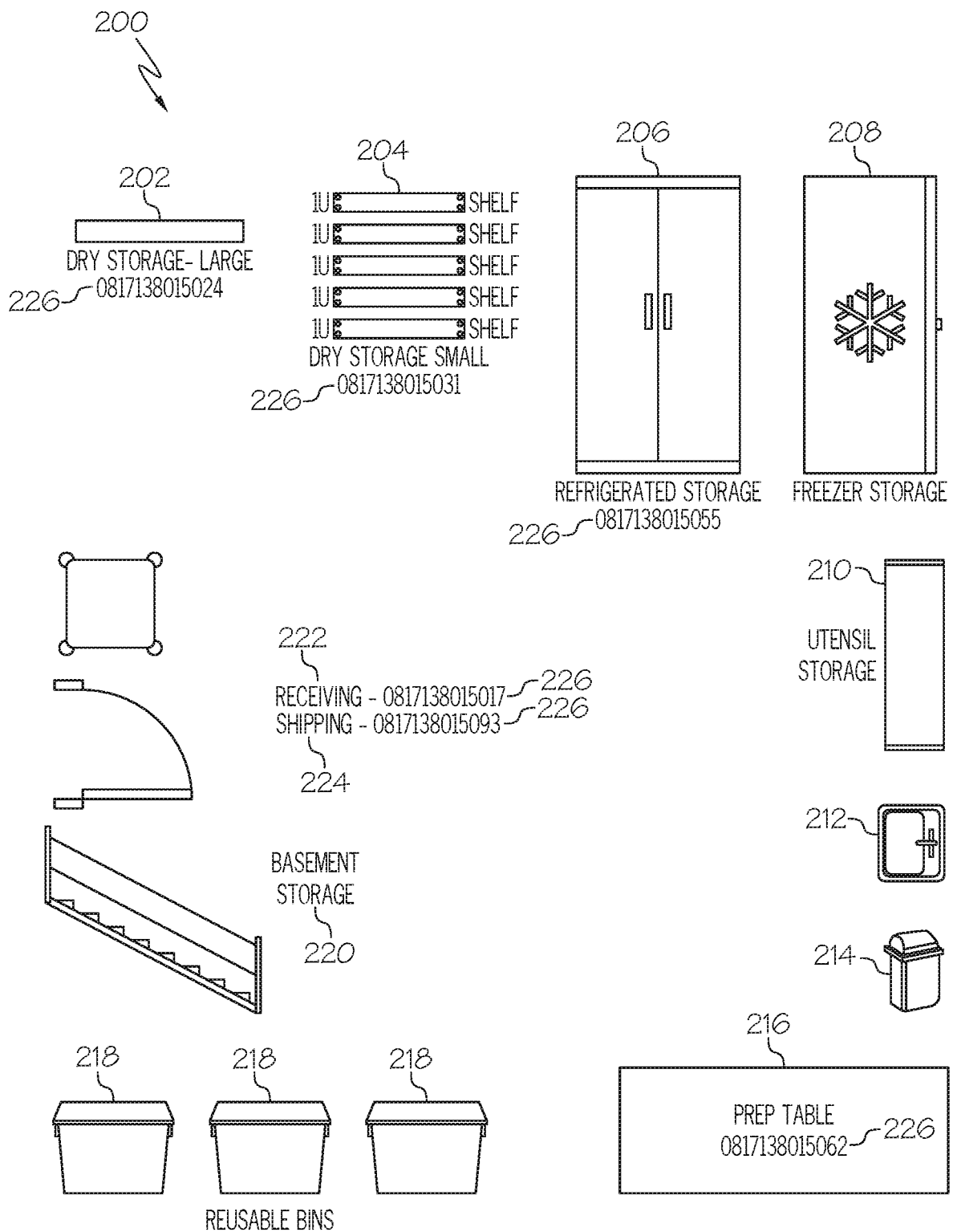
FIG. 2 illustrates a schematic view of one possible embodiment of a foodservice kitchen with locations uniquely identified in accordance with the disclosed architecture.

The innovation is now described with reference to the drawings, wherein like reference numerals are used to refer to like elements throughout. In the following description, for purposes of explanation, numerous specific details are set forth in order to provide a thorough understanding thereof. It may be evident, however, that the innovation can be practiced without these specific details. In other instances, well-known structures and devices are shown in block diagram form in order to facilitate a description thereof.

In one embodiment, the present invention discloses a method for food traceability from a food service location to the consumer. The method comprises marking the food product item with a label, and storing data from the label. Then, as food product items are received, a received label is generated and printed for the food product item. The received label identifies a storage location for the food product item and generates traceability information for the food product item. If the food product item is not intended for storage, then the food product item is transferred to a prep table and unique item information is generated for the food product item. The food product item can then be prepped for usage. During the prepping process, the food product item's expiration date is verified, and the food product item is weighed. A serial number is then generated and a "use by" date is calculated with respect to the prepped food product item. If the prepped food product item is to be served to a consumer, a label is generated with traceability information, and any unneeded ingredients from the prepped food product item are stored for future use, re-purposed or disposed of in a proper manner. Further, if the food product item's expiration date is verified and food product item is determined to be past its expiration date, the prepped food product item may be processed as donated food or properly disposed of as waste. Additionally, if the prepped food product item is not to be immediately served to a consumer, then the prepped food product item may be either stored or shipped to a desired location, thereby reducing waste and improving operational efficiencies in the food supply chain.

The present invention also discloses a method of receiving a food product item at a food service location, and tracing that food product item to either the consumer, an alternative user such as a donee, or its ultimate disposal as a waste. One of the first steps in the method of the present invention begins with the creation and setup of critical information, preferably in a comma delimitated or other suitable format, that can in turn be loaded into a food freshness printer 1800, such as the printer 1800 depicted in FIG. 19, or any other suitable printer as is known in the art. Critical information can be any information deemed necessary for food traceability, such as the various types of information 100 disclosed in FIG. 1. For example, FIG. 1 illustrates critical information 100 such as a vendor item number 102, a Global Trade Item Number (GTIN14) 104, a supplier name 106, an item description 108, a storage location 110, an order unit 112, a plurality of stored units 114, a shelf life 116, one or more inner packs 118, and a weight 120. It will be appreciated by one of ordinary skill in the art that the method of the present invention is not limited to the forgoing examples of critical information 100, and that other types of information, critical and non-critical, can also be included to suit user demand and/or preference.

FIG. 2 is a schematic view of one potential embodiment of a foodservice kitchen 200 with locations, such as those typically associated with food prep and/or storage, uniquely identified. For example, FIG. 2 discloses a relatively large area for dry storage 202, a small area for dry storage 204, a refrigerated storage 206, a freezer storage 208, a utensil storage 210, a sink 212, a trash receptacle 214, a prep table 216, a plurality of reusable bins 218, a basement storage area 220, a receiving area 222, and a shipping area 224. Each of the various areas in the kitchen 200 are identified with a unique number 226, which provides a user with complete visibility into the food product transformation trail, as described more fully below.

Figure 17:
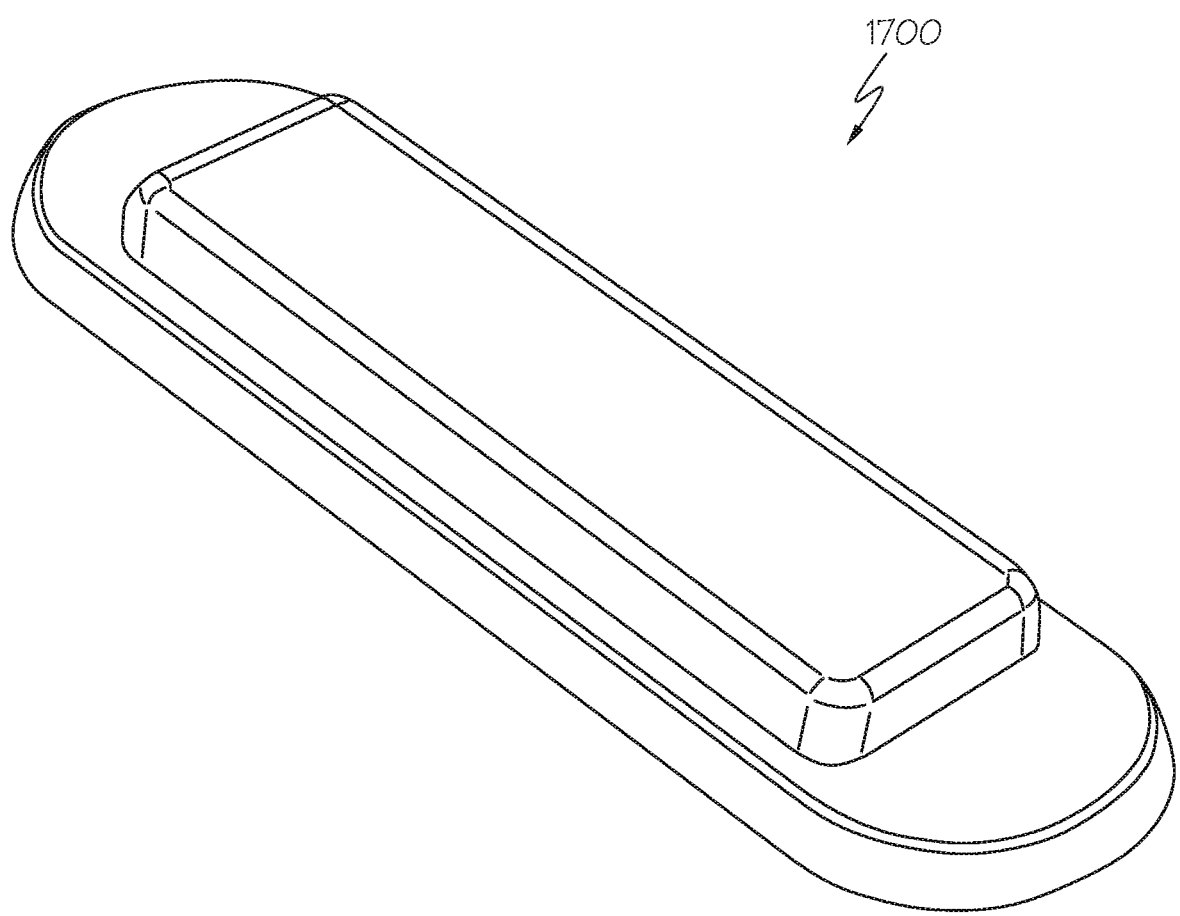
FIG. 17 illustrates a front perspective view of an RFID device in accordance with the disclosed architecture.
Figure 18:
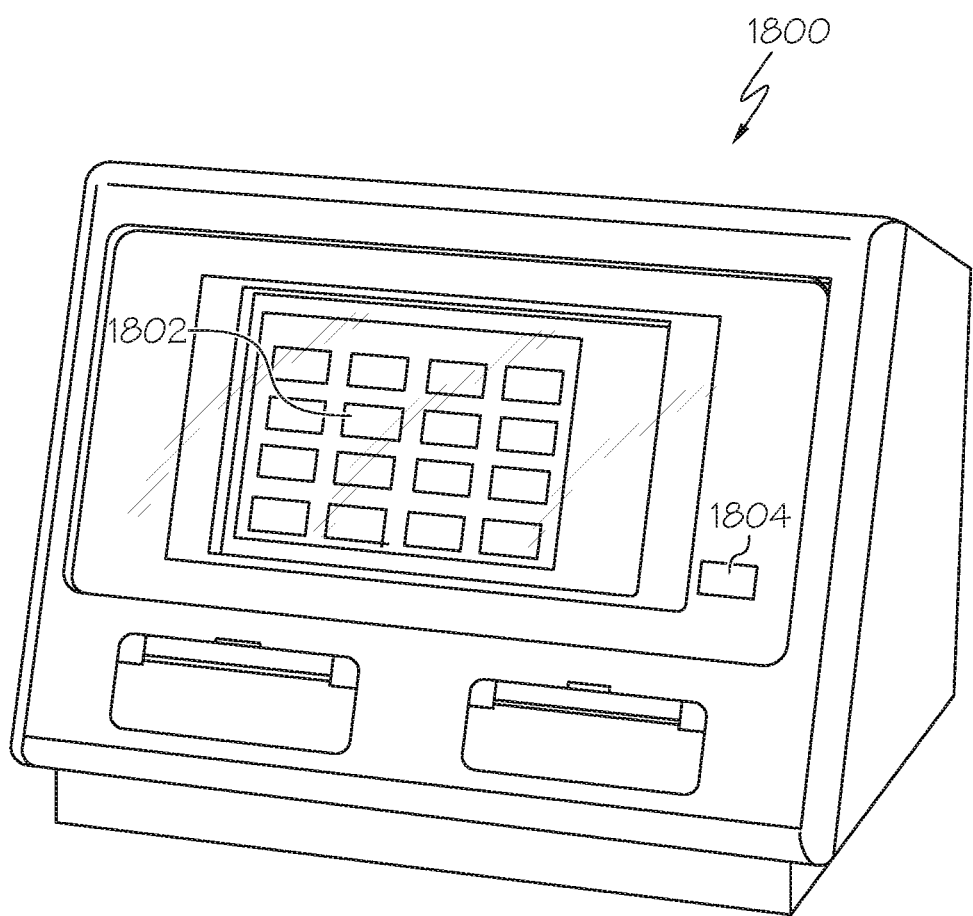
FIG. 18 illustrates a front perspective view of a food freshness printer in accordance with the disclosed architecture.

To initiate the process of food traceability, the user will receive incoming food products that are labelled, marked or otherwise tagged by an intelligent barcode printer 1800, such as the one depicted in FIG. 18. Printer 1800 is preferably equipped with a user display 1802, a barcode or QR code 1804 and/or an RFID reader 1700, such as the reader depicted in FIG. 17, or a smart device that is communicating with a barcode/RFID printer 1800, or any other suitable device as is known in the art. More specifically, the incoming food products are preferably marked with a label 500, such as the label shown in FIG. 5 which includes a food product or item name 502, a unique identifier or GTIN 504, a batch/lot number 506, a serial number 508, a product freshness date 510, a QR code 512, an item description 514, and other information that is deemed necessary or useful by a user. By way of example, the product freshness date 510 could be one of many dates indicating product freshness and/or useful life including, without limitation, a pack date, an expiration date, a "use by" date and/or a "best by" date. The label 500 could also be a RFID label, or any other suitable label or code that could be scanned in and recorded and/or linked to a webpage or database.

Figure 6:
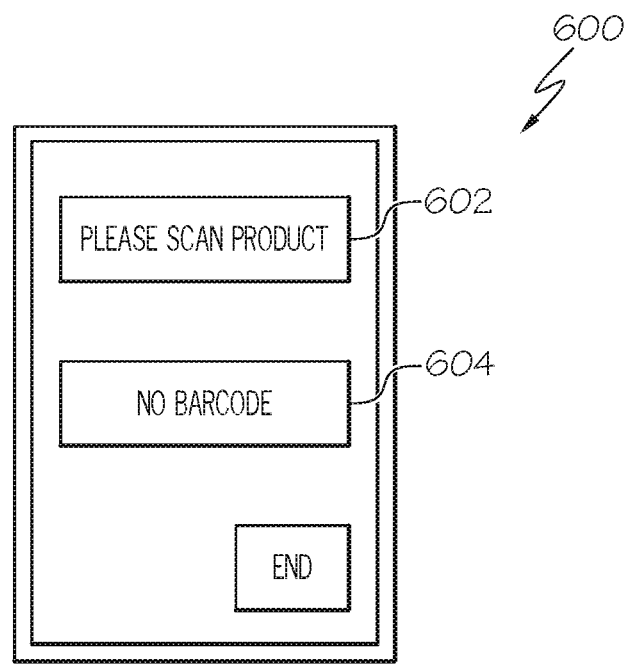
FIG. 6 illustrates a perspective view of a sample user interface for the receive process in accordance with the disclosed architecture.

An example of one embodiment of a user interface 600 is shown in FIG. 6, wherein the user is prompted to scan a food product item at 602. Scanning the food product item at 602 generates the traceability data in the background as a byproduct of normal printer functions but is less intrusive to the user. On the other hand, if the food product item is not already marked with a barcode 604, or other code such as a QR code, RFID tag, etc., the user will have the option to scan a code for the respective food product item from a scan book (not shown) to generate and print a receiving label for the food product item, or to input the necessary information to generate and print said label.

Figure 3:
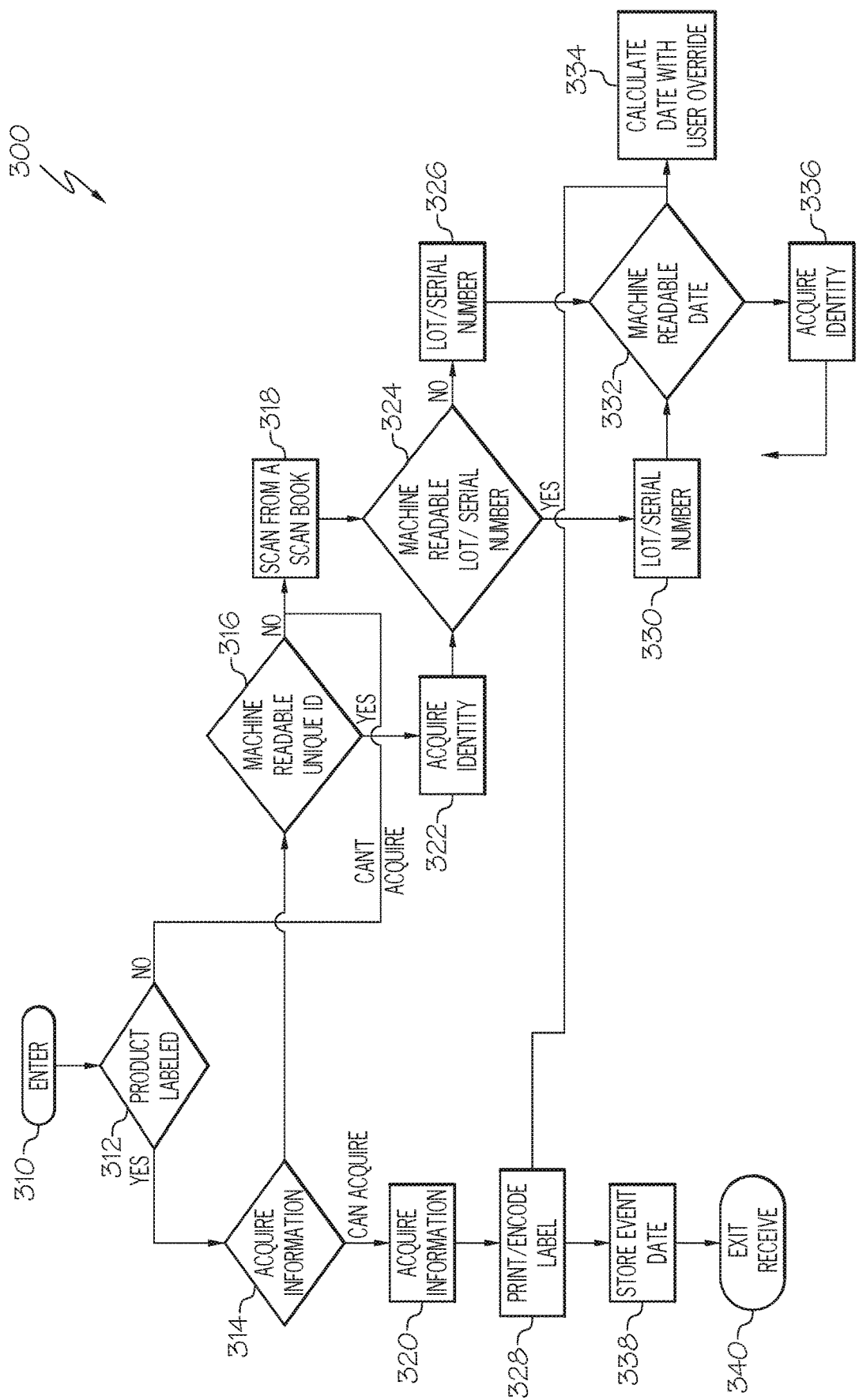
FIG. 3 illustrates a flowchart of one method for receiving the food product item in accordance with the disclosed architecture.

One possible example of the receive process 300 for food product items is generally depicted in FIG. 3. More specifically, the receive process 300 is initiated at 310 and a determination of whether the food product item is labelled is made at 312, for example, via the example user interface depicted in FIG. 6. If the food product item is labeled, then at 314 the label (e.g. barcode, QR code, RFID tag, etc.) is read to acquire the necessary product information for traceability purposes. If the data is successfully read from the label, then the data is acquired and stored at 320, and the process continues to print or encode the received label at 328. After the receive label is printed/encoded, at 338, event or EPCIS data is stored and the process exits the receive process 300 at 340. The event of EPCIS data is preferably in an industry standard format and can be later accessed for presentation in a dashboard for problem tracing. An example of such data 400 is shown in FIG. 4.

If, on the other hand, the product is not labelled at step 312 or information cannot be acquired at 314 (e.g., because the three critical elements: unique identification, product lot/serial number and date are not present in machine readable form (e.g., barcode, QR code, RFID, etc.)), the process 300 determines if each individual element can be machine read or, if not, an alternate data entry process is used. More specifically, at 316, the user looks for a machine readable unique identifier and, if one is present, the process continues to 322 to acquire the product identity. If there isn't a machine readable unique identity, then an identity may be scanned from a prepared scan book or other source at 318. The process then continues to 324 where it is determined if there is a readable product batch or serial number. If yes, the machine read of the lot/serial number occurs at 330 and, if not, the food product item may be assigned a unique serial number from a combination of the device ID and incrementing numbers at 326. Next, at 332, the user determines if there is machine readable data. If there is machine readable data, it is read at 336 and the identity of the food product item is acquired. If not, the user is prompted with the current date plus the food product useful life from, for example, the chart shown in FIG. 1 (see e.g., shelf life 116). The user can then override this date if required at 334.

Figure 5:
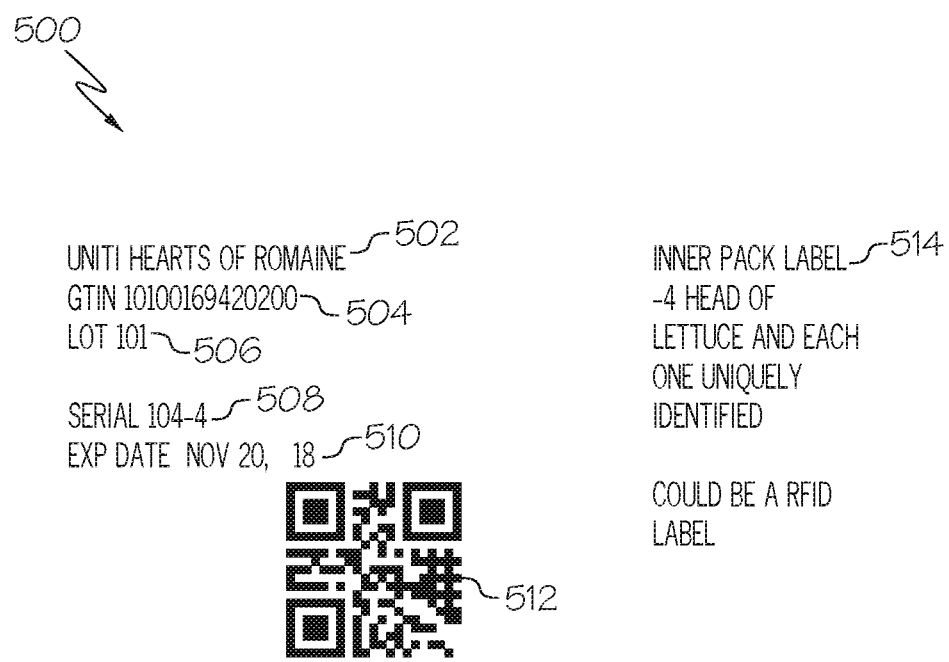
FIG. 5 illustrates an example of a receive label for a food product item in accordance with the disclosed architecture.

The receive process 336 then converges with the process from 320 at step 328 where the food product item is marked, and a label is printed or encoded. Specifically, using the data from the table in FIG. 1, the printer can now print/encode the appropriate number of inner pack labels, an example of which is depicted in FIG. 5. More specifically, the label 500 of FIG. 5 may comprise an item name 502, a GTIN number 504, a lot number 506, a serial number 508, an expiration or "best by" date 510, a QR code 512 and/or a description of the item 514. The label 500 could also be an RFID label or a barcode. The printer will then serialize the inner pack labels. The final step in the receive process is creating the event or EPCIS data for receiving shown at 338. As previously stated, this data is preferably in the industry standard format and can be later accessed for presentation in a dashboard for problem tracing, an example of which is shown at 400 in FIG. 4. The receive process then exits at 340.

The next sub-process in the food service traceable process is the "put away" process. Generally stated, the put away process is designed to be relatively simple for the user. In the initial configuration, the storage location for each unique food product item is identified. After the food product item is received by a user, the user is prompted as to whether to store the food product item or not. If yes, then the food product item is stored in the designated area and the traceability information is generated in the background. If the answer is no, then the food product item is transferred to the prep table with the unique item information generated in the background.

Figure 7:
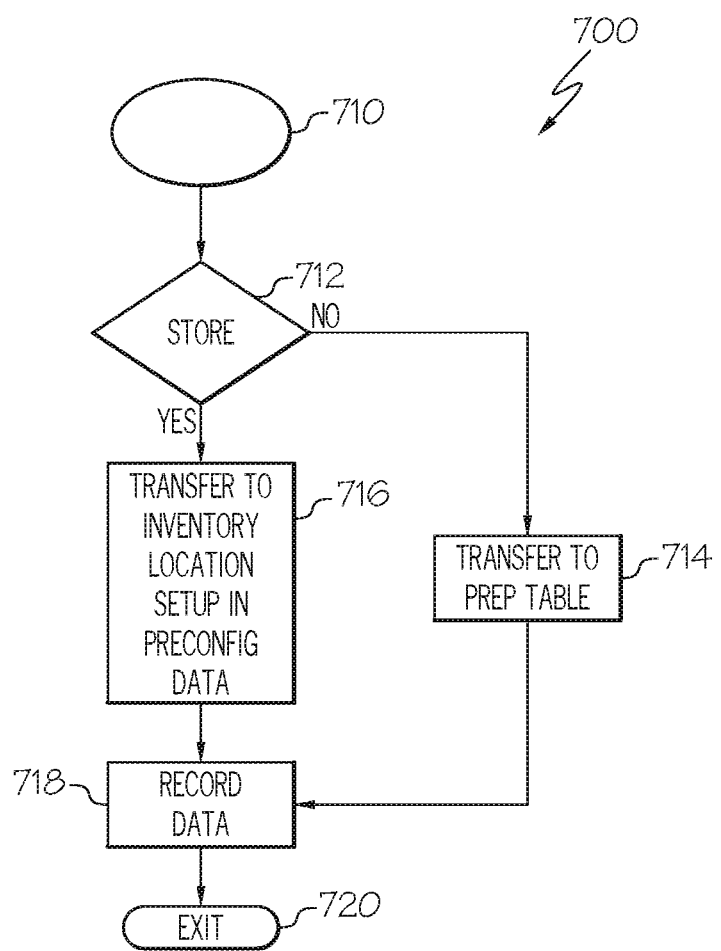
FIG. 7 illustrates a flowchart of one example of a method of processing a food product item in accordance with the disclosed architecture.

Specifically, the food product "put away" process 700 is illustrated at FIG. 7. The put away process initiates at 710 and proceeds to the decision at 712 as to whether to store the food product item or move the food product item directly to the prep table. If the food product item is to be stored, the necessary data for storage of the food product item is generated at 716. If, on the other hand, the food product item is not going to be stored, then the same is transferred to the prep table at 714. The two paths then converge at 718 where the necessary data is recorded and the process exits at 720. The inventory process highlights one of the advantages of using RFID technology in the process. For example, with RFID labeled inner packs and RFID readers mounted in the dry storage, the refrigerated storage, and the freezer storage, an up to date inventory with lot/serial numbers and relevant date information can be easily obtained and maintained.

The next sub-process in the food service traceable process is the transformation process, regardless of whether the transformation process produces an end food product for consumption or an intermediate product that will be used at a later time to produce an end food product for consumption. It is important to keep the following key data elements of the food product in place during the transformation process: the unique identity, the batch/serial number, and date. In the transformation process, an intelligent food process printer 1800, such as the one depicted in FIG. 18, is used to select the food product item to be prepped. The prepped food items are preconfigured by the user with the table 900 shown in FIG. 9 mapping the received food products into prepped food items. Similar to the received product list depicted in FIG. 1, the prepped food items preferably have a unique identifier and a "use by" date. The use by date should be no later in time than the last use by date from the prepped food items. As best depicted in FIG. 9, the prepped food product items can further comprise an input vendor/item number 902, a GTIN14 number 904, an item description 906, a storage location 908, a prep unit 910, a plurality of stored units 912, a shelf life 914, a plurality of inner packs 916, and a weight 918.

Figure 10:
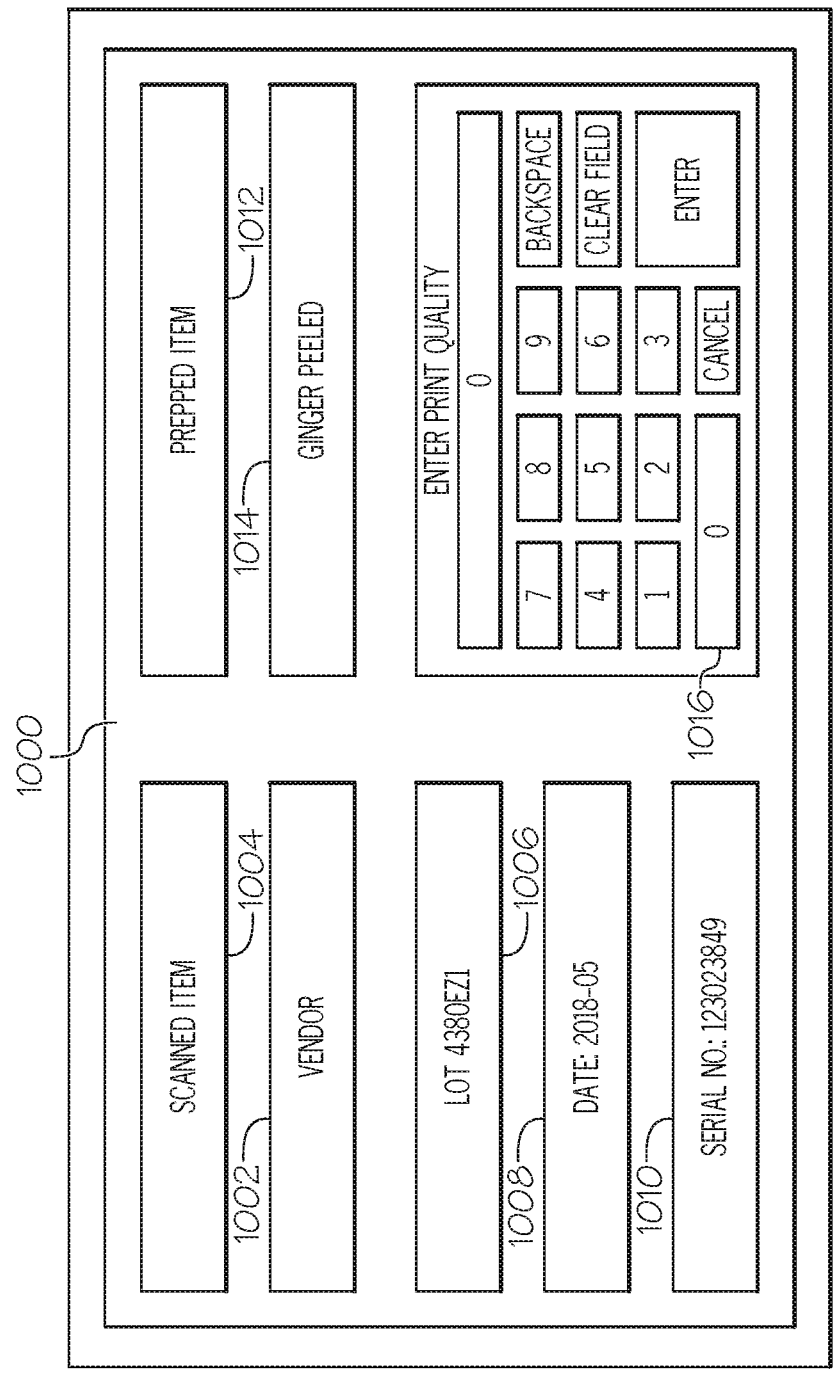
FIG. 10 illustrates a perspective view of one example of a user interface for prep food products in accordance with the disclosed architecture.

FIG. 10 depicts an example of a user interface and input screen. The input screen 1000 can be directly positioned on a food prep printer 1800, such as the printer depicted in FIG. 18, capable of printing barcodes and/or encoding RFID or on a smart device that can communicate with a printer capable of printing barcodes and/or encoding RFID intelligent labels. The user will select the food product item to prep, and then scan all of the items required to prep the food product item. Accordingly, the input screen 1000 would typically comprise an input for the scanned item 1002, a vendor designation 1004, a lot number 1006, a date 1008, a serial number 1010, a prepped item 1012, a description 1014, and a keypad 1016 for entering data in the various fields.

Figure 8A:
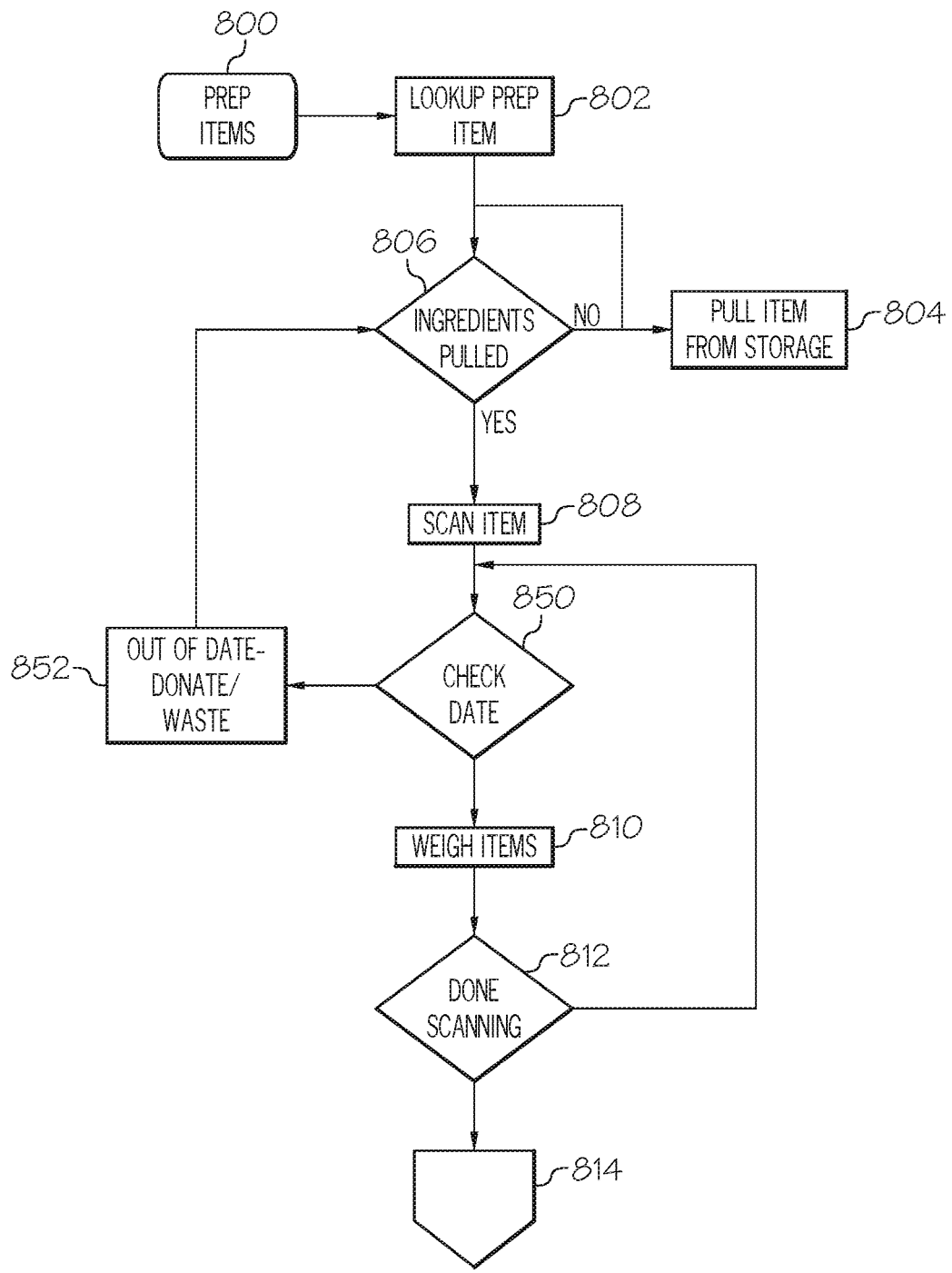
FIG. 8A illustrates a flowchart of the initial steps of one example of a method of transformation of the food product item in accordance with the disclosed architecture.
Figure 8B:
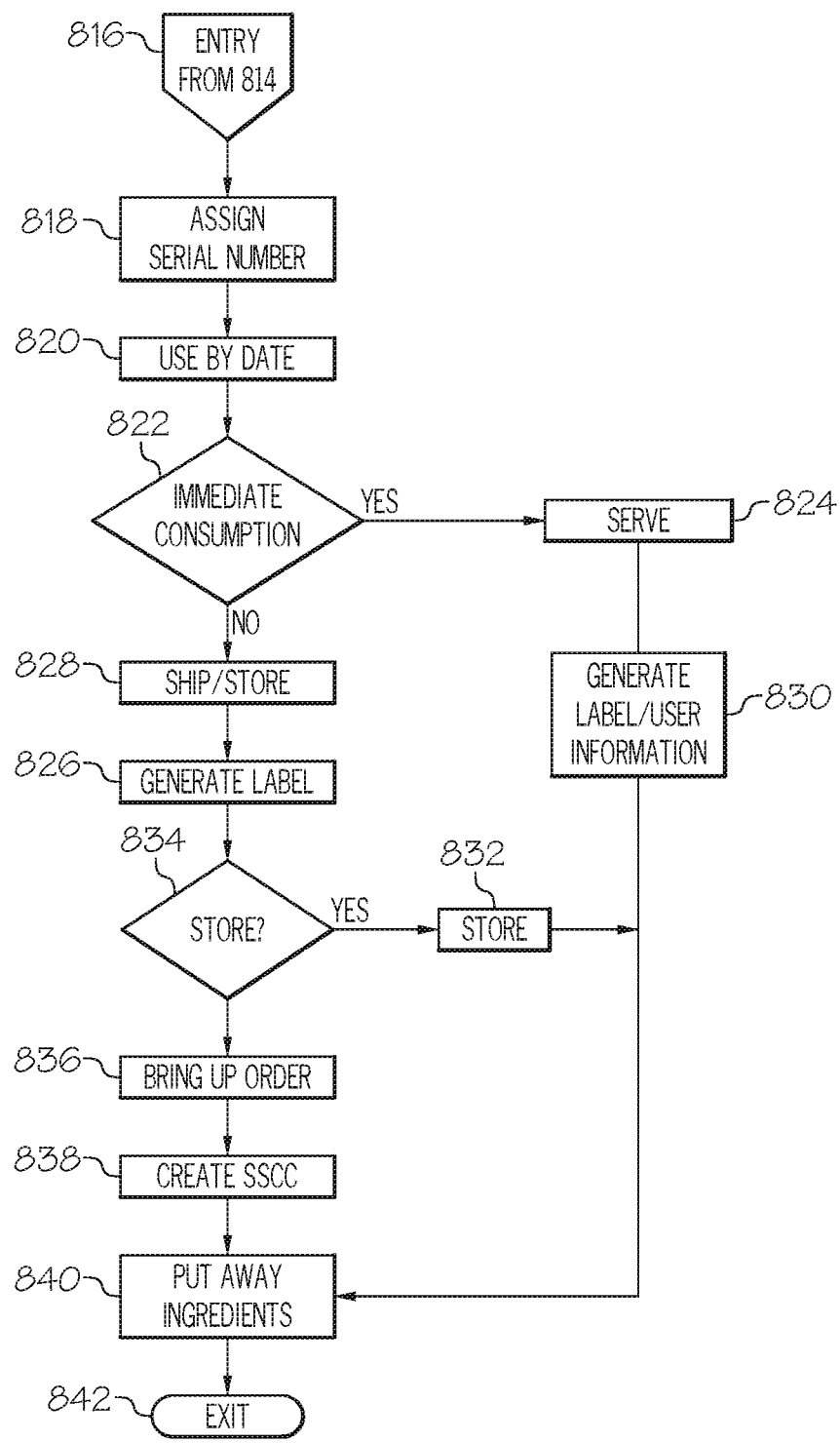
FIG. 8B illustrates a flowchart of the remaining steps of the method of transformation of the food product item of FIG. 8A in accordance with the disclosed architecture.

One potential embodiment of the transformation process is generally described in the flow chart depicted in FIGS. 8A and 8B and begins at 800 with a prepped food product item. At 802, the user looks up the food product item to be prepped. At 806, the user verifies that all of the food product item ingredients have been moved to the prep table, and at 808 the food items are scanned. At 850, the prep food product item ingredients are verified to ensure that sufficient time remains for it to be a viable ingredient. This verification is calculated by determining the remaining shelf life of the ingredient as compared to the desired shelf life of the prepped food product item. If there is not enough shelf life left to make the ingredient viable, then, at 852, the ingredient is processed for donation, re-purposing or properly disposed of as waste with the correct traceability information being generated, and the process returns to 806 to pull another inventory item.

Returning to step 850, if all of the necessary ingredients have been assembled and scanned and the dates verified at 850, then the user has the option of weighing the food product item at 810. If the food product item will not be consumed in the prep process, an accurate weight is required to maintain inventory. At 812, the item is done being scanned and the process exits to block 814 and enters the second half of the process depicted in FIG. 8B. If all of the items have not been assembled, then the path to 804 is followed to assemble and then verify the items/ingredients from storage. Additionally, in order to maintain the ease of use of the processes, the traceability information 1100 generated by the process depicted in FIG. 8A is concurrently being assembled in the background as depicted in FIG. 11 and includes the unique identifier along with the batch/serial number and relevant data of the items inputted into the transformation process. Next, the transformation process assigns a serial number and a "use by" date to the newly created item.

More specifically, as shown in FIG. 8B, the transformation process continues from block 814 to block 816. At 818, a serial number is generated and assigned to the food product item. The serial number is generated by the printer for the created item and is appropriate for, by way of example, both a 2D barcode and a RAIN RFID 96 bit SGTIN by combining a serialized counter stored in the application with a three-digit prefix for the device ID. Nonetheless, it is contemplated that other serial number generators can also be used to generate and assign serial numbers that satisfy user need and/or preference without affecting the overall concept of the present invention.

Figure 14:
FIG. 14 illustrates a front perspective view of one example of a card with traceability information that may be served with a food product item in a restaurant or other food service setting in accordance with the disclosed architecture.
Figure 16:
FIG. 16 illustrates a front perspective view of a web page for consumer food product information in accordance with the disclosed architecture.

At 820, a "use by" date is calculated for the prepped food product item by using the earlier of the shelf life shown in FIG. 11 for the item, or the ingredient used in the food product item with the earliest expiration date. At 822, the disposition of the prepped food product item is determined. More specifically, if the food product item is to be served to a consumer for immediate consumption, the path to 824 is followed and, at 830, a label is generated with the appropriate traceability information. An example of a label 1400 prepared for immediate end consumer consumption is depicted in FIG. 14, wherein the label 1400 preferably comprises a QR code 1402 and an item description 1404. Scanning the QR code 1402 on label 1400 will link the user or consumer to a web page 1600 containing the information depicted in FIG. 16, such as nutrition facts 1602, ingredient source 1604, and/or lot information 1606. Of course, other useful information can also be linked and provided to the user to suit user need or preference.

Figure 15:
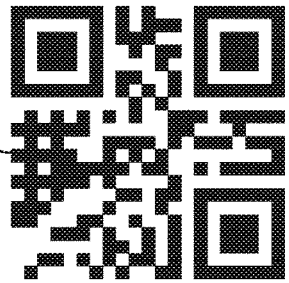
FIG. 15 illustrates a front perspective view of one example of a quick serve label with traceability information that may be served with a food product item in accordance with the disclosed architecture.

FIG. 15 also illustrates a front perspective view of one example of a quick serve label 1500 with traceability information that may be served with a food product item. The label 1500 preferably comprises a QR code 1502, an item description 1504, and nutrition information 1506. Scanning the QR code 1502 on label 1500 will also link the consumer to a web page 1600 containing the information shown in FIG. 16, or any additional information that may be desired, as disclosed above.

Returning now to FIG. 8B, after the label is generated, the process continues to 840 where the ingredients are put away. Specifically, putting the ingredient away preferably requires a weigh and scan out process. This process generates the traceability information moving the product back to the desired storage area. For example, if there are empty containers, then the user designates the scanned item as having been disposed of, and generates the appropriate traceability information. The process then exits at 842.

Figure 12:
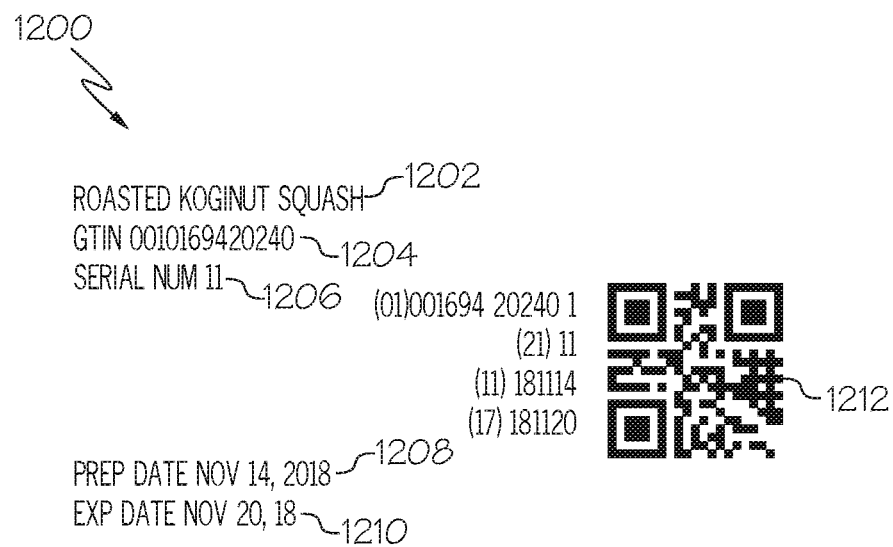
FIG. 12 illustrates a front perspective view of one example of a label for an intermediate food product item in accordance with the disclosed architecture.

Returning now to the immediate consumption decision at 822 in FIG. 8B, if the food product item is not to be immediately served to a consumer, then the process continues to 828 the ship/store process, and the item level label is generated at 826. An example of this type of label is generally depicted at 1200 in FIG. 12. Label 1200 is the same whether the food product item is stored or shipped and typically comprises a food product item name 1202, a GTIN number 1204, a serial number 1206, a prep date 1208, an expiration date 1210, and a QR code 1212 that could link the user to a webpage that displays additional information about the food product item, its sourcing, traceability, etc.

Figure 13:
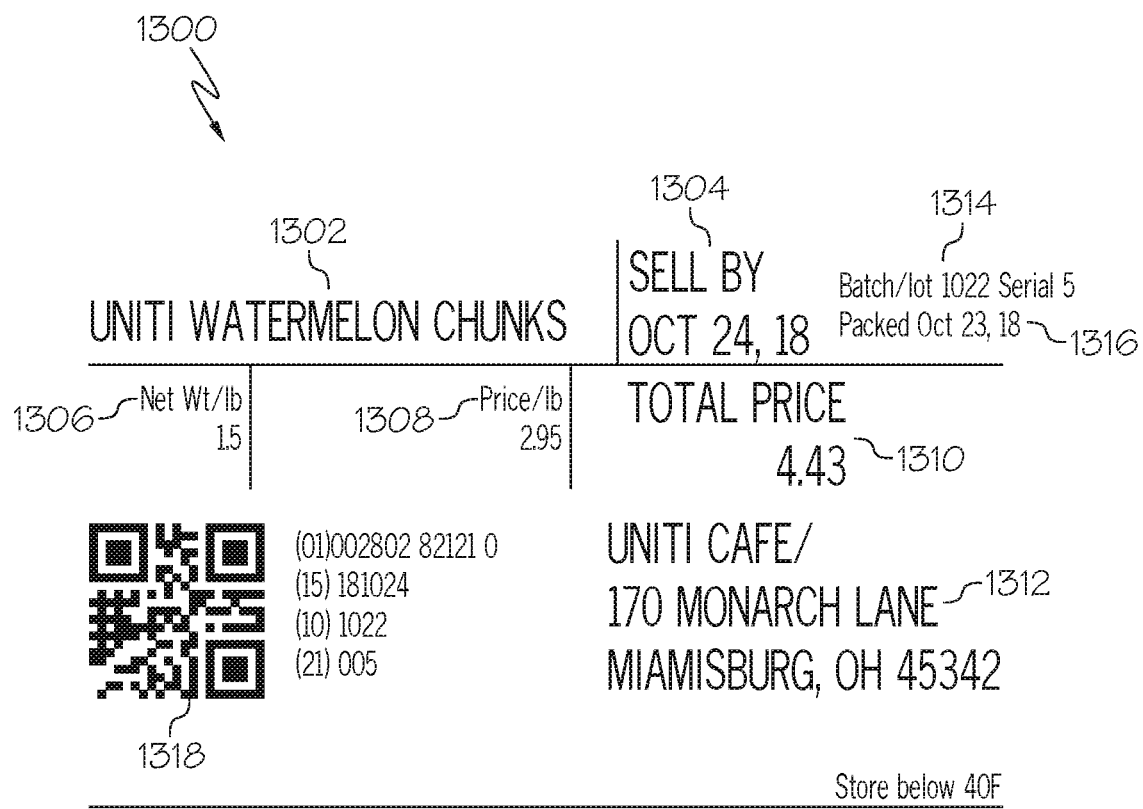
FIG. 13 illustrates a front perspective view of one example of a shipping label for a consumer food product item in accordance with the disclosed architecture.

As the transformation process continues in FIG. 8B, it is determined if the food product item is to be stored or shipped at 834. If the item is stored, the process continues to 832. The appropriate traceability information is then generated and the process continues to 840 where the ingredients are put away as disclosed above, and the process exits at 842. If, on the other hand, the food product item is to be shipped and not stored, then the process continues to 836 where the purchase order is brought up on the printer and the food product item is scanned and linked to the purchase order. This information will then be used to generate and advance a ship notice label. FIG. 13 discloses one possible example of shipping label 1300, which preferably comprises an item name 1302, a "sell by" date 1304, a new Wt./lb. 1306, a price/lb. 1308, a total price 1310, an address 1312, a batch/lot number 1314, a packed date 1316, and a QR code 1318 that could link the user to a webpage that displays additional information about the food product item, its sourcing, traceability, etc. If the order is complete at 838, a serial shipping container code (SSCC) and an advance ship notice (ASN) are generated and the process continues to 840 where the ingredients are put away as disclosed above, and the process exists at 842. In a further embodiment of the method of the present invention, an alert can be generated to the party currently in possession of the food product item or ingredient when the expiration date is nearing or has passed, thereby reducing the likelihood that an expired food product item will be consumed.

What has been described above includes examples of the claimed subject matter. It is, of course, not possible to describe every conceivable combination of components or methodologies for purposes of describing the claimed subject matter, but one of ordinary skill in the art may recognize that many further combinations and permutations of the claimed subject matter are possible. Accordingly, the claimed subject matter is intended to embrace all such alterations, modifications and variations that fall within the spirit and scope of the appended claims. Furthermore, to the extent that the term "includes" is used in either the detailed description or the claims, such term is intended to be inclusive in a manner similar to the term "comprising" as "comprising" is interpreted when employed as a transitional word in a claim.

What is claimed is:

1. A method of tracing a product from an origin to an ultimate disposition:
   receiving, by a printer having an input screen, at least one item having a first set of data linked thereto;
   generating, by the printer, a second set of data linked to the product, using the first set of data;
   generating, by the printer, traceability information about the product, using the first and second sets of data;
   prepping the at least one item to create a prepped item;
   calculating a relevant date for the prepped item;
   generating a serial number for the prepped item;
   updating the traceability information for the prepped item; and
   generating a digital ID with the updated traceability information contained therein.

2. The method of claim 1 further comprising transforming the at least one item into the product using the printer.

3. The method of claim 1, wherein the relevant date indicates an expiration date for the prepped item.

4. The method of claim 1 further comprising providing the traceability information about the product to a user.

5. The method of claim 1, wherein the ultimate disposition of the product is one of a consumer consumption, a re-purposing or a disposal.

6. The method of claim 1, wherein the first set of data comprises a shelf life for each of the at least one item and the second set of data comprises a relevant date for the product.

7. The method of claim 6, wherein the shelf life for each of the at least one item is used to calculate the relevant date for the product.

8. The method of claim 6 further comprising using the relevant date to generate an alert about the product to the user.

9. The method of claim 4, wherein the user indicates one of a merchant, a customer or a supply chain partner.

10. The method of claim 1, wherein the traceability information comprises one or more of the following: (a) a list of ingredients of the product; (b) a source of the list of ingredients; (c) an identifying number for the product; and (d) a relevant date for the food product.

11. The method for tracing an item from a service location to a consumer comprising:
    assigning, via an input screen of a printer, a set of critical information to the item, upon receiving the item at the service location;
    generating, by the printer, traceability information relative to the item, using the set of critical information;
    encoding, by the printer, the traceability information in a digital ID;
    prepping the at least one item to create a prepped item;
    calculating a relevant date for the prepped item;
    generating a serial number for the prepped item;
    updating the traceability information for the prepped item; and
    generating a digital ID with the updated traceability information contained therein.

12. The method of claim 11, wherein the set of critical information comprises one or more of the following relative to the item: (a) a vendor identifier; (b) an identification number; (c) a description; (d) a storage location; (e) a shelf life; and (f) a weight.

13. The method of claim 11, wherein the traceability information comprises one or more of the following relative to the item: (a) a list of ingredients; (b) a source of each of the list of ingredients; (c) an identifying number; and (d) a relevant date.

14. The method of claim 11, wherein the generated digital ID comprises one of a barcode, an RFID driven digital ID or a QR code.

15. The method of claim 11 further comprising assigning an initial destination to the item and including the initial destination in the traceability information.

16. The method of claim 15, wherein the initial destination is one of the consumer, a storage location or a shipping location.

17. The method of claim 13 further comprising using the relevant date to generate an alert about the item for the consumer.

18. A method for tracing an item:
   upon receiving a item with a digital ID, reading, by a reader in communication with a printer, the digital ID to obtain information about the item;
   encoding, by the printer, the received digital ID for the item;
   identifying, by the printer, an initial location for the item;
   generating, by the printer, traceability information for the item;
   prepping the at least one item to create a prepped item;
   calculating a relevant date for the prepped item;
   generating a serial number for the prepped item;
   updating the traceability information for the prepped item; and
   generating a digital ID with the updated traceability information contained therein.

19. The method of claim 18, wherein when the initial location for the item is a storage location, the method further comprises designating the storage location and including the storage location in the traceability information.

20. The method of claim 18 further comprising using the relevant date to generate an alert about the prepped item for a user.

21. The method of claim 18 further comprising encoding the traceability information for the item in the digital ID.

22. A method of tracing a product from an origin to an ultimate disposition:
   receiving, by a printer having an input screen, at least one item having a first set of data linked thereto;
   generating, by the printer, a second set of data linked to the product, using the first set of data;
   generating, by the printer, traceability information about the product, using the first and second sets of data, wherein the first set of data comprises a shelf life for each of the at least one item and the second set of data comprises a relevant date for the product, and
   wherein the shelf life for each of the at least one item is used to calculate the relevant date for the product;
   prepping the at least one item to create a prepped item;
   calculating a relevant date for the prepped item;
   generating a serial number for the prepped item;
   updating the traceability information for the prepped item; and
   generating a digital ID with the updated traceability information contained therein.

* * * * *